United States Patent [19]

Gross

[11] Patent Number: 4,553,551
[45] Date of Patent: Nov. 19, 1985

[54] LIFTING BELT

[75] Inventor: Clifford M. Gross, New York, N.Y.

[73] Assignee: Hospital for Joint Diseases Orthopedic Institute, New York, N.Y.

[21] Appl. No.: 466,919

[22] Filed: Feb. 16, 1983

[51] Int. Cl.$^4$ ............................................. A41C 1/00
[52] U.S. Cl. ................................................. 128/567
[58] Field of Search ............... 2/44, 338; 128/78, 66, 128/578, 95, 567

[56] References Cited

U.S. PATENT DOCUMENTS

| 1,753,739 | 4/1930 | Burns | 128/567 |
| 3,194,234 | 7/1965 | Duckman et al. | 128/578 |

Primary Examiner—Doris L. Troutman
Attorney, Agent, or Firm—Stephen E. Feldman

[57] ABSTRACT

A longitudinally extending section of elastic material of predetermined width is secured to one end to an end of a longitudinally extending section of relatively non-elastic material to form therewith a body encircling lifting belt. A plurality of bendable stays are secured in pockets formed along one surface of said belt and so as to extend across the width thereof; a pair of said stays being carried by said elastic section, one of said stays being disposed at the place where said elastic section is secured to said non-elastic section, and five such stays being carried by said non-elastic section. Two additional torsion support stays, are disposed in longitudinally extending pockets each positioned between a pair of said other stays to form therewith a pair of spaced "H" shaped torsion supports. The torsion supports being carried by said belt for disposition one to each side of the spine of the person wearing the belt, and in proximity to their lumbar and pelvic body areas. As such, the belt when worn will reduce spinal stress, transmit stress from the lumbar area to the pelvic, reduce the speed at which the wearer can bend, and prevent excessive twisting of the wearer's torso, when lifting and performing other materials handling tasks.

18 Claims, 3 Drawing Figures

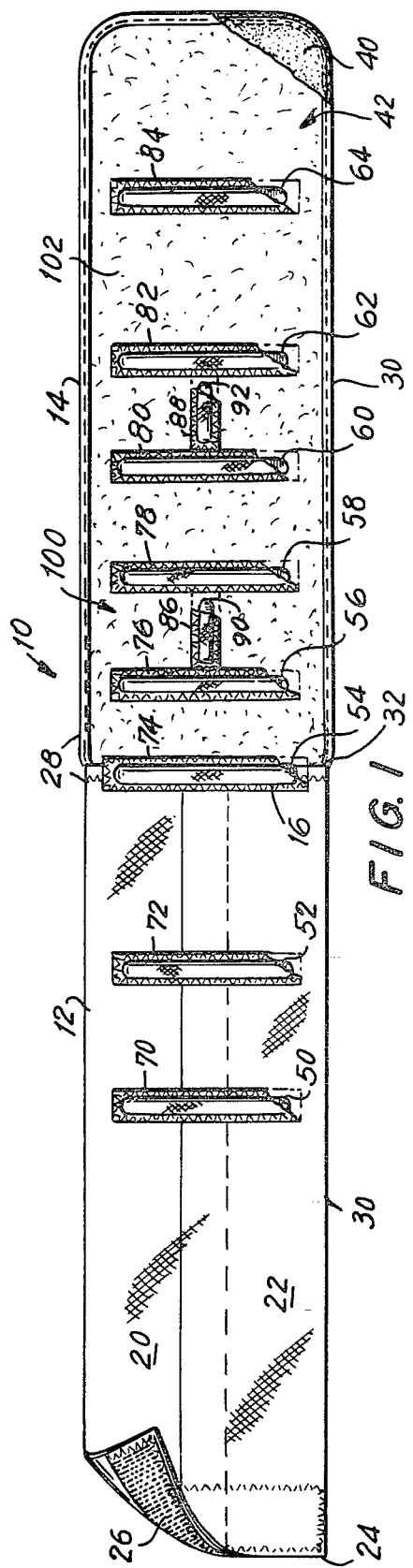
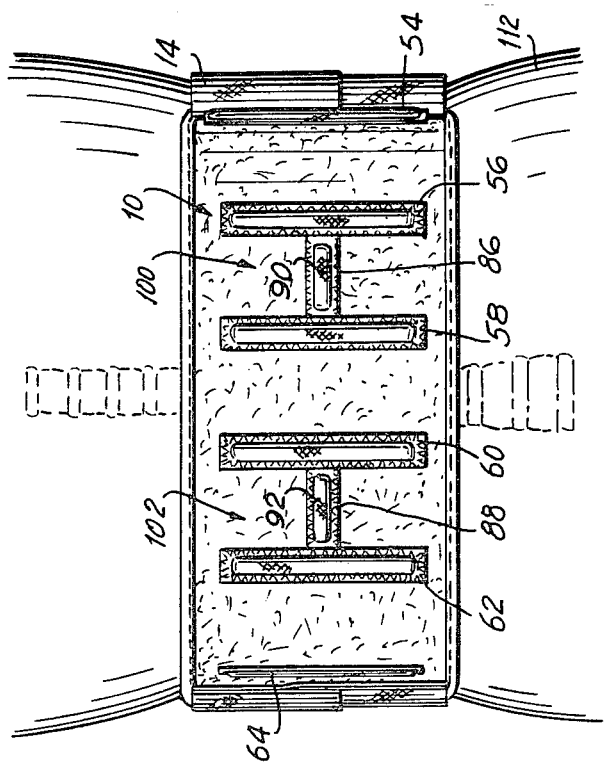
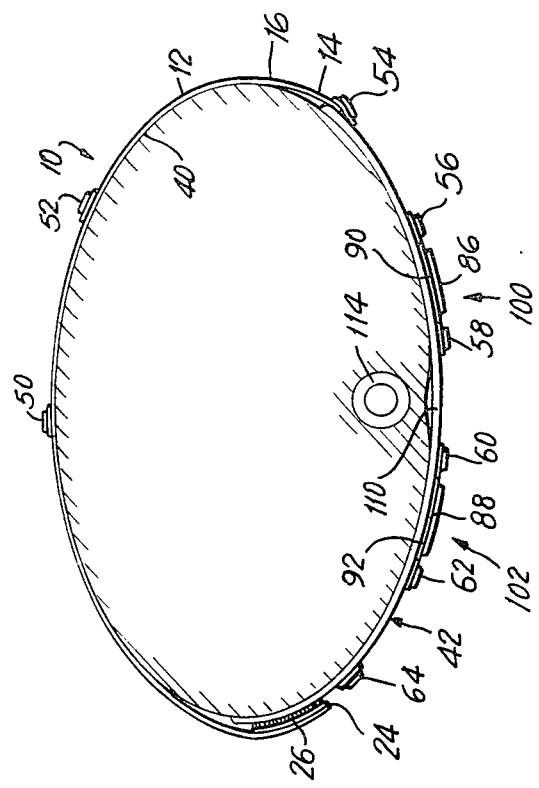

LIFTING BELT

BACKGROUND OF THE INVENTION

1. Field of Application

This invention relates to body encircling belts; and more particularly to belts for encircling and for providing support to a particular area of the human body.

2. Description of the Prior Art

A great many types and kinds of belt-like devices exist for encircling and providing support to and for particular areas of the human body. However, the great majority of such belts are for corrective rather than preventive purposes. Some such belts are designed to urge one or more body parts back into their normal position. Others are constructed to restrict movement of a body part to prevent further injury thereto, or pain resulting from an unwanted movement of a previously injured body member. Still other belts function to compress or rearrange sagging body members to help slim and beautify the figure. Very few, if any, available belt-like devices are constructed or intended to prevent body strain, stress, or injury during work.

A significant number of such belt-like devices are categorized as medical corsets, orthopedic garments or support belts. Some such belt-like devices are shown on: U.S. Pat. No. 2,372,034 granted on Mar. 20, 1964 to I. R. Versoy for Supporting Belt And Ptosis Pad; in U.S. Pat. No. 3,570,480 granted on Mar. 16, 1971 to F. F. Stubbs for Medical Corset; and in U.S. Pat. No. 3,578,773 granted on May 18, 1971 to A. L. Schultz for Supportive Orthopedic Device. Devices such as these are utilized to urge a particular part of the human body, such as an organ located in the abdominal cavity, back into its original position following weakening of the muscles after surgery or an accident. Not only are these devices relatively complex in construction and cumbersome to use, but they only find utility after the body part is no longer maintained in its usual body position by normal body muscles. Their construction is such that a person in need of the corrective features of the device would probably be physically incapable of any significant lifting or material handling tasks. Persons not in need of the corrective features of these devices would find it difficult, if not impossible, to adapt same for use while performing lifting of material handling tasks, since the inherent construction of these belts would most likely inhibit rather than facilitate use of the very muscles, and other members of the human body, required for such tasks.

Others of such belt-like devices ar shown in U.S. Pat. No. 4,175,553 granted on Nov. 27, 1979 to H. W. Rosenberg for Lumbosacral-Orthosis Orthopedic Support and in U.S. Pat. No. 4,245,625 granted on Jan. 20, 1981 to J. Eichler for Back Support Device. Such belts incorporate rigid metal plate-like components, and are used to brace and support an injured back or spine against unwanted movement which, if not prevented, could result in great pain and further injury. These belts are also usually worn by persons who are physically incapable of performing lifting or other material handling tasks. A person who is physically able to do such work would probably not find this type of belt helpful because their rigidity could hinder breathing during work, and otherwise restrict use of the needed body members while not properly supporting them.

Still other belt-like supports, such as shown in U.S. Pat. No. 3,812,862 granted on May 28, 1974 to B. L. Bernstein for Waist Supporting Garment, are intended to improve the human figure by compressing, squeezing and re-arranging same to compensate for deteriorating muscle tone and strength brought on by age, gaining weight and lack of proper exercise. This type of belt would be totally unsuitable to support the human body during work which required a significant amount of lift and movement.

Weight lifters will at times use a belt of the type shown in U.S. Pat. No. 4,348,774 granted on Sept. 14, 1982 to T. W. Woodson for Weight Lifter's Belt. However, the leather belt construction dictates use of a relatively narrow waist encircling member so that the user can breathe properly; and does not facilitate cleanability which would be required of a device that must be worn daily during strenuous work.

SUMMARY OF THE INVENTION

It is therefore an object of this invention to provide a new and improved lifting belt.

It is another object of this invention to provide a new and improved body encircling belt which provides passive lumbar support.

It is yet another object of this invention to provide a new and improved body encircling belt that reduces spinal stress during lifting and other material handling tasks.

It is yet still another object of this invention to provide a new and improved body encircling belt that facilitates transfer of stress from the lumbar area to the pelvis.

It is yet still a further object of this invention to provide a new and improved body encircling belt which provides some degree of torsional rigidity for the users torso to prevent excessive twisting thereof during lifting and while performing other material handling tasks.

This invention involves a body encircling belt for use by persons who are physically capable of performing lifting and other strenuous material handling tasks. It contemplates forming the body encircling belt of material which is washable, and which will breathe while worn to facilitate its use throughout an entire working day; while at the same time providing body members support elements at selected locations on the belt, to generate a bending stress to which the user is responsive and which induces the user to bend at a slower rate thus reducing the possibility of back injury, to facilitate transmitting stress generated while performing tasks from upper lumbar regions to the pelvis, and to provide torsional rigidity for the users torso and prevent excessive twisting thereof.

Other objects, features, and advantages of the invention in its details of construction and arrangement of parts will be seen from the above, from the following description of the preferred embodiment when considered with the drawing and from the appended claims.

BRIEF DESCRIPTION OF THE DRAWING

In the drawing:

FIG. 1 is a plan view of a body encircling lifting belt incorporating the instant invention and cut away in part to better show details thereof;

FIG. 2 is a schematic; in horizontal section, illustrating the lifting belt of FIG. 1 disposed about the appropriate portion of a users body; and FIG. 3 is a schematic, partial vertical showing, illustrating the lifting belt of FIG. 1 disposed as shown in FIG. 2.

For convenience, the invention will be described as applied to a lifting belt of a length or longitudinal extent sufficient to encircle the body of the user proximate the lumbar/pelvis region thereof, and of a height or width sufficient to overlay the users lumbar area and at least a portion of the pelvis. The belt is fabricated with one-half of its length formed of stretchable elastic material in two parallel bands which overlap along their length a predetermined amount; and with the other half of its length formed of flannel backed. foam-like material. The two-halves are sewn together. A VELCRO type fastener is applied to a predetermined section of the elastic material proximate its free end and coacts with the flannel portion of the other half of the belt to secure the belt in its body encircling position. A number of bendable support stays (formed of suitable metal) are sewed into pockets formed at selected positions along the length of the belt; their being two such stays carried by the elastic section of the belt, one stay where the elastic and non-elastic section of the belt are sewn together, and seven stays carried by the non-elastic section of the belt. Of the seven stays one is disposed proximate the free end of the non-elastic belt section and the other six are arranged in two "H"-shaped torsion compensating support sections. As utilized, the great majority of the support stays extend across the width (or height) of the belt from a place proximate one longitudinal edge to a place proximate the other longitudinal edge; with the stays that form the horizontal bars of the "H"-shaped torsion support sections spanning their respective vertically extending stays proximate their mid-points. It should be understood, nevertheless, that without departing from the scope of this invention: that the stretchable belt section may be formed of any suitable stretchable material and in either one single band, or multiple bands appropriately secured together; that the non-stretchable belt section may be fabricated from any suitable material which will breathe to facilitate user wearing and which is washable to facilitate cleaning; that the securing means can be any available means; and that the number of support stays and their relative disposition can be varied as along as there are at least a pair of torsion compensating support sections carried by the belt for disposition one to each side of the wearer's spine at the lumbar region.

With respect to FIGS 1–3 there is generally shown at 10 a lifting belt formed with a stretchable section 12 and a non-stretchable section 14 secured together, as by sewing at 16.

Stretchable section 12 is fabricated from two bands 20, 22 of material which will stretch in at least the longitudinal direction. The material for section 12 may be elastic, Lycra, or the like, with bands 20, 22 connected together at their ends by sewing or other suitable process. If desired bands 20, 22 may be connected together at other areas along their respective overlapping portions. Stretchable section 12 has a free end 24 to one surface of which is secured a section 26 of Velcro type fastening elements, and a pair of spaced longitudinally extending edges 28, 30. Another end 32 of stretchable section 12 is secured to non-stretchabe section 14 by sewing or other suitable means.

Non-stretchable section 14 is formed so that one of its surfaces 40 is fabricated from a material such as foam or the like. The criteria for the material of surface 40 is that the material must feel comfortable when disposed against the body of the person wearing lifting belt 10 and the material must breathe so as to facilitate being worn throughout the day by a person who is performing lifting and other mechanical tasks. The other surface 42 of section 14 can be fabricated from flannel or any other material which will coact with Velcro type fasteners 26 to secure sections 12 and 14 together in a body encircling condition. The materials selected for stretchable section 12 and non-stretchable section 14 must also be readily washable.

A plurality of support stays 50, 52, 54, 56, 58, 60, 62 and 64 are secured in pockets 70, 72, 74, 76, 78, 80, 82 and 84 respectively formed at selected positions along the longitudinal extent of belt 10. Pockets 70–84 may be formed of any suitable material and to a size and configuration sufficient to cover support stays 50–64. Pockets 70–84 are formed by sewing pieces of such material along their edges to the underlying materials of belt 10. Pockets 70–84 extend across the width of belt 10 terminating short of longitudinal edges 28, 30 thereof. Two additional pockets 86, 88 are disposed so as to extend longitudinally between pockets 76, 78 and 80, 82 respectively; stays 90 and 92 are disposed in pockets 86, 88 respectively. It should be noted that stays 56, 90, 58 and that stays 60, 92, 62 each form a torsion support section 100, 102 respectively for purposes to be hereinafter explained. While an "H"-shaped configuration has been shown for torsion support sections 100, 102 it should be realized that other configurations which stiffen belt 10 in its longitudinal direction will function just as well as to support the wearer against unwanted torsional movement of the torso, as will be hereinafter explained.

Stays 50–64, 90 and 92 are formed from a suitable bendable metal such as a lightweight spring steel. However, suitable plastic strips or strips of other spring type bendable material may be used.

The user may wear lifting belt 10 with the foam side 40 (the side opposite to the one carrying stays 50–64, 90 and 92) disposed either against their body or against a T shirt, athletic shirt or the like. Belt 10 is wrapped around the user's body so as to cover the lumbar region 110 (FIGS. 2 and 3) of the user's back and so as to extend between same and the user's pelvic region 112 (FIG. 3). Torsion support sections 100, 102 of belt 10 are to be disposed so that one such section is to one side of the wearer's spine 114 (FIGS. 2 and 3) and so that the other such section is to the other side of the user's spine 114. Stretchable section 12 is then stretched to provide a comfortable fit and VELCRO type fastener 26 is secured to material 42 to close belt 10. When so disposed stays 50 and 52 will be positioned over the user's stomach and stays 54 and 64 will be appropriately positioned around the user's body.

Belt 10 is thus fabricated and stays 50–64, 90 and 92 positioned to provide a lifting belt which will facilitate lifting and materials handling tasks. When so worn at least stays 50 and 52 will provide a selected degree of support and stiffness so that when the wearer of belt 10 is bending over from the waist that a bending stress will be generated. As such, the stress will prevent the user from bending over rapidly and thus prevent or minimize back injuries which might otherwise result from bending movements.

Stays 54–64 facilitate transmission of stress from the wearer's lumbar region 110 to their pelvic region 112 providing the wearer with an added increment of support. While torsion support sections 100, 102 provide a selected degree of torsional rigidity for the wearer of belt 10 to prevent excessive twisting of the user's torso when lifting and performing materials handling tasks.

From the above description, it will thus be seen that there has been provided a novel and improved lifting belt which is simple in construction, and easy to wear and which when worn during lifting and/or while performing materials handling tasks: will facilitate transmission of spinal stress from the lumbar region of the wearer to their pelvic area to reduce spinal stress during lifting; will generate an anti- stress to induce the wearer to bend at a slower rate; and will provide a degree of torsional rigidity to prevent excessive twisting of the wearer's torso.

It is understood that although I have shown the preferred form of my invention that various modifications may be made in the details thereof without departing from the spirit as comprehended by the following claims.

I claim:

1. A lifting belt; comprising:
    (a) body encircling belt means;
    (b) said body encircling belt means including only a first section and a second section, said first section being formed of relatively stretchable material and said second section being formed of relatively non-stretchable material;
    (c) said first section and said second section being secured together at respective attaching ends to provide a belt of predetermined length and width and which has a first free end a second free end and opposed spaced longitudinally extending side edges;
    (d) a plurality of bendable support means carried by said body encircling belt means and disposed at selected positions in spaced relationship with respect to each other along the longitudinal extent thereof and so as to extend from proximate one of said side edges to proximate the other of said side edges;
    (e) said positions of said bendable support means being selected so that when said belt means is worn about the waist of a person and proximate their lumbar and pelvic regions that at least first predetermined ones of said plurality of bendable support means tend to prevent rapid bending of a person wearing said belt means, and so that at least second predetermined ones of said plurality of bendable support means transmit at least some of the spinal stress of the wearer to the wearer's pelvic area; and
    (f) securing means disposed proximate one of said free ends of said belt means for coaction with said other of said free ends of said belt means to secure same in body encircling position about a person.

2. The weight lifting belt of claim 1, wherein a first selected number of said plurality of bendable support means together form a first torsion support section and a second selected number of said plurality of bendable support means together from a second torsion support section; said first torsion support section and said second torsion support section being positioned on said belt means and spaced thereon from one another so that when said belt means is worn by a person one such torsion support section is disposed to one side of the person's spine and the other of said torsion support sections is disposed to the other side of the person's spine; both said torsion support sections co-operating when so disposed to prevent excessive twisting of the person's torso.

3. The lifting belt of claim 2, wherein each of said torsion support sections include at least one bendable support means from said plurality of bendable support means and a bendable torsion support disposed at a predetermined angle with respect thereto.

4. The lifting belt of claim 3, wherein said predetermined angle is ninety degrees.

5. The lifting belt of claim 4, wherein said bendable torsion support for each of said torsion support sections extends from proximate one bendable support means to proximate a next adjacent bendable support means.

6. The lifting belt of claim 5, wherein said torsion support sections are spaced one from the other.

7. The lifting belt of claim 1, wherein said first section of said belt means is formed from a pair of members each formed of elastic material and which are secured together in overlapping relationship along their longitudinal extent.

8. The lifting belt of claim 7, wherein said second section of said belt means is formed of a composite material one side of which is a foam type material and the other side of which is a flannel type material.

9. The lifting belt of claim 8, wherein at least a pair of said plurality of bendable support means are carried by said first section of said belt means, and another of said plurality of bendable support means is disposed where said first sections of said belt means is secured to said second section of said belt means.

10. The lifting belt of claim 1, wherein said first and said second predetermined angles is ninety degrees.

11. The lifting belt of claim 9 wherein additional bendable support means are carried by said second section of said belt means and there are at least five other bendable support means carried by said second section of said belt means with a first pair of said five other bendable support means and a first one of said additional support means forming a first torsion support, and with a second pair of said five other bendable support means and a second one of said additional bendable support means forming a second torsion support; said first one of said additional support means being disposed between and at a first predetermined angle with respect to said first pair of bendable support means, and said second one of said additional support means being disposed between and at a second predetermined angle with respect to said second pair of bendable support means.

12. A weight lifting belt; comprising:
    (a) body encircling belt means;
    (b) said body encircling belt means including a first section formed of relatively stretchable material and a second section formed of relatively non-stretchable material;
    (c) said first section and said second section being secured together at respective attaching ends to provide a belt of predetermined length and width and having a first free end a second free end and opposed spaced longitudinally extending side edges;
    (d) a plurality of bendable support means carried by said body encircling belt means and disposed at selected positions in spaced relationship with each other along the longitudinal extent thereof and so as to extend from proximate one of said edges to proximate the other of said edges;
    (e) said positions of said bendable support means being selected, so that when said belt means is worn about the waist of a person and proximate their lumbar and pelvic regions that at least first predetermined ones of said plurality of bendable support stays tend to prevent rapid bending of a person wearing said belt means, and so that at least second predetermined ones of said plurality of bendable support means transmit at least some of the spinal stress of the wearer to the wearer's pelvic area;

(f) securing means disposed proximate one of said free ends of said belt means for coaction with said other of said free ends of said belt means to secure same in body encircling position about a person;

(g) a first selected number of said plurality of bendable support means together forming a first torsion support section and a second selected number of said plurality of bendable support means together forming a second torsion support section;

(h) said first torsion support section and said section torsion support section being positioned on said belt means and spaced thereon from one another so that when said belt means is worn by a person one such torsion support section is disposed to one side of the person's spine and the other of said torsion support sections is disposed to the other side of the person's spine; both said torsion support sections co-operating when so disposed to prevent successive twisting of the person's torso;

(i) each of said torsion support sections including at least one bendable support means, from said plurality of bendable support means, and a bendable torsion support disposed at an angle of ninety degrees with respect thereto.

13. The lifting belt of claim 12, wherein said bendable torsion support for each of said torsion support sections extends from proximate one bendable support means to proximate a next adjacent bendable support means.

14. The lifting belt of claim 13, wherein said torsion support sections are spaced one from the other.

15. The lifting belt of claim 12, wherein said first section of said belt means is formed from a pair of members each formed of elastic material and which are secured together in overlapping relationship along their longitudinal extent.

16. The lifting belt of claim 15, wherein said second section of said belt means is formed of a composite material one side of which is a foam type material and the other side of which is a flannel type material.

17. The lifting belt of claim 16, wherein at least a pair of said plurality of bendable support means are carried by said first section of said belt means, and another of said plurality of bendable support means is secured to said second section of said belt means.

18. The lifting belt of claim 17 wherein there are at least five other bendable support means carried by said second section of said belt means with a first pair of said five other bendable support means and one of said bendable torsion support forming said first torsion support section and with a second pair of said five other bendable support means and another of said bendable torsion support forming said second torsion support section.

* * * * *